(12) United States Patent
Moskalev et al.

(10) Patent No.: US 7,129,349 B2
(45) Date of Patent: Oct. 31, 2006

(54) METHODS OF SYNTHESIZING 3-AMINO-1,2,4-BENZOTRIAZINES

(75) Inventors: Nikolai V. Moskalev, Claremont, CA (US); Gordon W. Gribble, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 10/528,090

(22) PCT Filed: Oct. 8, 2003

(86) PCT No.: PCT/US03/31988

§ 371 (c)(1),
(2), (4) Date: Sep. 22, 2005

(87) PCT Pub. No.: WO2004/034023

PCT Pub. Date: Apr. 22, 2004

(65) Prior Publication Data

US 2006/0142569 A1    Jun. 29, 2006

Related U.S. Application Data

(60) Provisional application No. 60/417,569, filed on Oct. 10, 2002.

(51) Int. Cl.
  *C07D 253/10* (2006.01)
  *A61K 31/53* (2006.01)
  *A61P 31/04* (2006.01)
  *A61P 33/06* (2006.01)

(52) U.S. Cl. .................................... 544/183; 514/243

(58) Field of Classification Search ................. 544/183
See application file for complete search history.

(56) References Cited

U.S. PATENT DOCUMENTS 5,175,287 A    12/1992    Lee et al. ................... 544/183

*Primary Examiner*—Venkataraman Balasubramanian
(74) *Attorney, Agent, or Firm*—Licata & Tyrrell P.C.

(57) ABSTRACT

An improved method of producing 3-amino-1,2,4-benzotriazines using nitrobenzene or a derivative thereof, a guanidine salt and a base as reactants is provided. The method is carried out at a moderate reaction temperature without producing halide wastes derived from nucleophilic substitution and acid byproducts.

1 Claim, No Drawings

METHODS OF SYNTHESIZING 3-AMINO-1,2,4-BENZOTRIAZINES

This application is a 371 of PCT/US03/31988 filed Oct. 08, 2003, which claims benefit of U.S. Provisional Application No. 60/417,569 filed Oct. 10, 2002.

BACKGROUND OF THE INVENTION

3-Amino-1,2,4-benzotriazines are heterocyclic compounds that have diverse applications in the both the agrochemical and pharmaceutical industries. These compounds were originally found to have antimicrobial activity (DE 2204574; DE 2740887; and U.S. Pat. Nos. 3,980,779; 3,868,371; 3,991,189; 3,957,799 and 4,001,410) and have since been shown to have herbicidal (DD 272591; Henrie, et al. (1993) Quant. Struct. Act. Relat. 12:27–37), antimalarial (Horner and Henry (1968) J. Med. Chem. 11:946–949), human blood reology regulant (Boehme (1988) Med. Reihe 37:123–124), antifungal (Reich, et al. (1989) J. Med. Chem. 32:2474–2485), and antiinflammatory and analgesic (Regan, et al. (1980) J. Pharm. Sci. 69:798–793) activities. Of particular interest are the 3-amino-1,2,4-benzotriazine oxide derivatives that are used as radiosensitizers and selective cytotoxic agents for the treatment of tumors (U.S. Pat. No. 6,362,184; WO 01/46162; WO 89/08647; WO 91/04028; Dorie and Brown (1993) Cancer Res. 53:4633–4636; Kelson, et al. (1998) Anti-Cancer Design 13:575–592; Brown (2000) Molecular Medicine Today 6:157–162; Denny and Wilson (2000) Expert Opinion on Invest. Drugs 9:2889–2901).

Common methods for the synthesis of 3-amino-1,2,4-benzotriazines include the thermal reaction of 2-nitroaniline with cyanamide (Mason and Tennant (1970) J. Chem. Soc. 911), the base-induced cyclization of 2-nitrophenylurea followed by treatment with phosphoryl chloride and gaseous ammonia (Arndt (1913) Chem. Ber. 46:3522), and the addition of disodiocyanamide to benzofuroxan followed by acidic workup (U.S. Pat. No. 3,980,779; Seng and Ley (1972) Angew. Chem., Int. Ed. Engl. 11:1009). Alternative steps may include, for example, peracid oxidation of the parent monoxide of 1,2,4-benzotriazine to produce the dioxide (Robbins, et al, (1957) J. Chem. Soc. 3186; Mason, et al, (1970) J. Chem. Soc. B 911) and monoxide preparation by controlled reduction of the corresponding dioxide (Mason, et al, (1970) J. Chem. Soc. B 911; Wolf, et al. (1954) J. Am. Chem. Soc. 76:355). 3-Amino-1,2,4-benzotriazines may also be prepared by cyclization of formazan precursors using $BF_3$/AcOH (Atallah and Nazer (1982) Tetrahedron 38:1793). Furthermore, o-fluoronitrobenzenes may be reacted for 4–6 hours with free guanidine base at 60° C. in t-BuOK/THF (Suzuki and Kawakami (1997) Synthesis 855) to produce these compounds.

The disadvantage of many of these methods is the production of halide wastes, acid byproducts, and the use of highly toxic corrosive substances at high temperatures. Given the commercial potential of 3-amino-1,2,4-benzotriazines, a need exists for a practical, safe, high yielding, and direct synthetic process for the manufacture of such compounds.

SUMMARY OF THE INVENTION

The present invention provides a method for producing 3-amino-1,2,4-benzotriazines. The method comprises combining a nitrobenzene or a derivative thereof with a guanidine salt in the presence of a base at moderate temperature. These and other aspects of the present invention are set forth in more detail in the following description of the invention.

DETAILED DESCRIPTION OF THE INVENTION

The present invention relates to an improved method of synthesizing 3-amino-1,2,4-benzotriazine compounds. In contrast to prior methods of synthesizing 3-amino-1,2,4-benzotriazines, the method provides a simple, safe, straightforward one-step method which produces the product in a high yield. In general, the method of the invention, comprises combining nitrobenzene or a derivative thereof (1), a guanidine salt (2), and a base at moderate temperature to produce a 3-amino-1,2,4-benzotriazine (3). This general method is depicted below in Scheme 1.

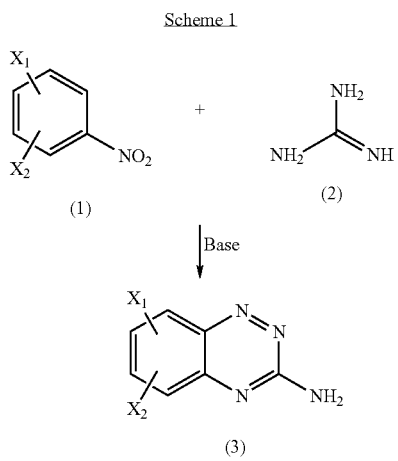

The $X_1$ and $X_2$ of the nitrobenzene reactant (1) are independently the same or different and are preferably hydrogen; a nitro group; a cyano group; a halogen (e.g., fluorine, chlorine, bromine, or iodine); a hydroxyl group; or an alkyl group (1–14C; e.g., methyl, ethyl, i-propyl, n-propyl, n-butyl, n-pentyl, n-heptyl and the like). When alkyl, $X_1$ or $X_2$ may be substituted or unsubstituted, cyclic or acyclic, branched or unbranched, and may optionally be interrupted by a single ether linkage.

The alkyl $X_1$ and $X_2$ groups may optionally be substituted with 1 or 2 substituents selected from a halogen such as fluorine, chlorine, bromine or iodine; hydroxy; epoxy; alkoxy(1–6C) such as, for example, methoxy, ethoxy, n-propoxy, isopropoxy, isobutoxy, pentoxy, hexoxy and t-butoxy; alkyl thio; (1–4C) primary amino ($NH_2$); morpholino; pyrrolidino; piperidino; secondary amino (NHR'); tertiary amino (NR'R'); acyloxy and acylamido groups represented by R'COO— and R'CONH—, respectively, and their thiol analogs represented by R'CSO— and R'CSNH—, respectively; carboxy(—C(O)OH); alkoxycarbonyl (—C(O)OR'); carbamyl (—C(O)$NH_2$); alkylcarbamyl (1–4C)(—C(O)NHR'); alkylsulfonyl (1–4C) ($R'SO_2$—); and alkyl phosphonyl (1–4C) (R'P(OR')O—); where R' is a 1–4C alkyl, such as methylamino, propylamino and the like.

In addition, $X_1$ and $X_2$ may each independently be —$NH_2$, —NHR', —NR'R', —OCOR', —NH(CO)R', —O(SO)R' or —O(POR')R' in which the various R' groups are lower alkyls (1–4C) which themselves may be substituted with OH, $NH_2$, alkyl secondary and tertiary amino, pyrrolidino, piperidino, alkoxy (1–4C), or halogen substituents.

Representative guanidine salts useful in the present invention include, but are not limited to guanidine hydrochloride, guanidine carbonate or sulfate salts and the like. Guanidine hydrochloride is preferred.

The reaction may be carried out in a single aprotic bipolar solvents or a mixture of aprotic bipolar solvents. Aprotic bipolar solvents useful in the method of the present invention include but are not limited to solvents such as dimethylformamide (DMF), dimethylacetamide (DMAc), acetonitrile, dimethylsulfoxide (DMSO), hexamethylphosphorus triamide (HMPA), tetramethylurea, N-methylpyrrolidone and the like.

The base may be added prior to or after the addition of the nitrobenzene to the guanidine salt.

Suitable bases that can be used in accordance with the method of the present invention include those capable of accepting protons during the course of a reaction. Examples of such bases include, but are not limited to, alkali metal alkoxides such as potassium 3,7-dimethyl-3-octanoxide, potassium isopropoxide, potassium n-butoxide, sodium methoxide, potassium n-propoxide, potassium t-amylate, sodium 3,7-dimethyl-3-octanoxide, sodium isopropoxide, sodium n-butoxide, sodium n-hexylate, sodium n-propoxide, sodium t-amylate, sodium t-butoxide sodium ethoxide, and potassium t-butoxide and dialkylamides such as lithium diisopropylamide. The base may be selected routinely by those of skill in the art in accordance with these teachings based upon the nature of the reactants, the solvent or solvents in which the reaction is conducted, and the temperature at which the reaction is conducted. The amount of base used is generally 2.0 mol to 10.0 mol, preferably 6 mol, per 1 mol of nitrobenzene or a derivative thereof.

The reaction temperature is generally moderate from about −30° C. to about 100° C. Preferably the reaction temperature is from about 15° C. to 20° C. The reaction time is generally 20 minutes to 12 hours. Preferably the reaction time is 20 to 30 minutes.

The reaction mixture is then treated to induce precipitation (also referred to as quenching) of the 3-amino-1,2,4-benzotriazine. This may be accomplished using a variety of compounds including, but not limited to ammonium salts, such as ammonium chloride, ammonium sulfate, or ammonium nitrate; acetic acid; or 5–15% hydrochloric acid. Following quenching, the precipitate comprising the the 3-amino-1,2,4-benzotriazine is recovered. The reaction conditions yield at least about 10%, preferably at least 40%, of the desired 3-amino-1,2,4-benzotriazine reaction product.

The quenched reaction may be further purified by extraction three to four times with ethyl acetate, drying over sodium sulfate, filtering, and evaporating to remove the solvent. The resulting composition may be recrystallized or separated by flash chromatography using, for example, silica gel with a hexane:ethyl acetate (2:1) solvent, to obtain product of at least 95% purity.

The 3-amino-1,2,4-benzotriazines produced by the method of the invention may be further oxidized according to well-known methods in the art (Robbins, et al, (1957) J. Chem. Soc. 3186; Mason, et al, (1970) J. Chem. Soc. B 911; Mason, et al, (1970) J. Chem. Soc. B 911; Wolf, et al. (1954) J. Am. Chem. Soc. 76:355) to produce monoxide or dioxide derivatives including, but not limited to, 3-amino-1,2,4-benzotriazine 1-oxide; 3-amino-1,2,4-benzotriazine 1,4-dioxide (Tirapazamine); 3-amino-7-decyl-1,2,4-benzotriazine 1-oxide; 3-amino-7-trifluoromethyl-1,2,4-benzotriazine 1-oxide; 3-amino-7-carbamyl-1,2,4-benzotriazine 1-oxide; and 3-amino-6(7)-decyl-1,2,4-benzotriazinel, 4-dioxide. Alternatively, the 3-amino-1,2,4-benzotriazine products may be in situ methylated, for example, by addition of excess methyl iodide to produce 3-N,N-dimethylamino derivatives or may be alkylated according to known methods (DD 272591; WO 88/02366) to produce 3-N-alkyl or 3-N,N-dialkyl derivatives.

The invention is described in greater detail by the following non-limiting examples.

EXAMPLE 1

Preparation of 3-Amino-1,2,4-Benzotriazine

To a stirring mixture of guanidine hydrochloride (160 mg, 1.7 mmol) and t-BuOK (670 mg, 6 mmol) in DMSO (4 mL) was added one portion of nitrobenzene (123 mg, 1 mmol) at room temperature. The mixture turned red in one minute. In 20 to 30 minutes the mixture was quenched with a saturated, aqueous solution of ammonium chloride. A yellow precipitate was formed and removed by filtration. The precipitate was then washed with water, dried in the air, and recrystallized from benzene or ethanol to give 105 mg (72%) of 3-amino-1,2,4-benzotriazine. The melting point was determined to be 203–205° C., consistent with the melting point (207° C.) of 3-amino-1,2,4-benzotriazine synthesized by other known methods (J. Chem. Soc. (B) (1970) 911).

EXAMPLE 2

Preparation of Substituted 3-Amino-1,2,4-Benzotriazines

Similar to the preparation of 3-amino-1,2,4-benzotriazine, other substituted 3-amino-1,2,4-benzotriazines were synthesized from a mixture of guanidine hydrochloride (1.7 mmol) and a nitrobenzene derivative (1 mmol). t-BuOK (6 mmol) in DMSO (45 mmol) was added to the reactants at room temperature. The mixtures turned red, were quenched with a saturated, aqueous solution of ammonium chloride, and yellow precipitates were formed and removed by filtration. The precipitates were then washed with water, dried in the air, and recrystallized from benzene or ethanol providing the yields indicated in Table 1.

TABLE 1

| Reactant Product | Yield |
| --- | --- |
| 3-amino-6-fluoro-1,2,4-benzotriazine | 35% |
| 3-amino-6-chloro-1,2,4-benzotriazine | 56% |
| 3-amino-6-methoxy-1,2,4-benzotriazine | 50% |
| 3-amino-8-chloro-1,2,4-benzotriazine | 46% |

The melting point of 3-amino-6-chloro-1,2,4-benzotriazine was determined to be 275–277° C., consistent with the melting point (275–277° C.) of 3-amino-6-chloro-1,2,4-benzotriazine synthesized by other well-known methods (Synthetic Commun. (1976) 6:457).

What is claimed is:

1. A method of producing a 3-amino-1,2,4-benzotriazine compound comprising combining a nitrobenzene of the structure

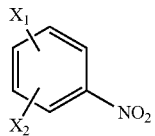

wherein $X_1$ and $X_2$ are independently the same or different and are a hydrogen; a nitro group; a cyano group; a halogen; a hydroxyl group; —NH$_2$; —NHR'; —NR'R'; —OCOR', —NH(CO)R', —O(SO)R' or —O(POR')R', wherein R' is a substituted or unsubstituted lower alkyl; or an alkyl group, wherein said alkyl is substituted or unsubstituted, cyclic or acyclic, branched or unbranched, or interrupted by a single ether linkage, with a guanidine salt in the presence of a base at a moderate reaction temperature to produce a 3-amino-1,2,4-benzotriazine.

* * * * *